United States Patent
Fichtinger et al.

(10) Patent No.: US 11,756,689 B2
(45) Date of Patent: Sep. 12, 2023

(54) PROFICIENCY ASSESSMENT SYSTEM AND METHOD FOR DEEP BRAIN STIMULATION (DBS)

(71) Applicants: UNIVERSITÉ DE RENNES 1, Rennes (FR); INSERM—INSTITUT NATIONAL DE LA SANTÉ ET DE LA RECHERCHE MÉDICALE, Paris (FR); CENTRE HOSPITALIER UNIVERSITAIRE PONTCHAILLOU, Rennes (FR); QUEEN'S UNIVERSITY, Kingston (CA)

(72) Inventors: Gabor Fichtinger, Kingston (CA); Matthew Holden, Kingston (CA); Pierre Jannin, Rennes (FR); Claire Haegelen, Montgermont (FR); Yulong Zhao, Rennes (FR)

(73) Assignees: UNIVERSITÉ DE RENNES 1, Rennes (FR); INSERM—INSTITUT NATIONAL DE LA SANTÉ ET DE LA RECHERCHE MÉDICALE, Paris (FR); CENTRE HOSPITALIER UNIVERSITAIRE PONTCHAILLOU, Rennes (FR); QUEEN'S UNIVERSITY, Kingston (CA)

( * ) Notice: Subject to any disclaimer, the term of this patent is extended or adjusted under 35 U.S.C. 154(b) by 455 days.

(21) Appl. No.: 16/754,089

(22) PCT Filed: Oct. 9, 2018

(86) PCT No.: PCT/EP2018/077446
§ 371 (c)(1),
(2) Date: Apr. 6, 2020

(87) PCT Pub. No.: WO2019/072829
PCT Pub. Date: Apr. 18, 2019

(65) Prior Publication Data
US 2020/0335221 A1    Oct. 22, 2020

(30) Foreign Application Priority Data
Oct. 11, 2017    (EP) .................................... 17306370

(51) Int. Cl.
*G16H 50/50*    (2018.01)
*G16H 40/60*    (2018.01)
*A61N 1/05*    (2006.01)

(52) U.S. Cl.
CPC ............. *G16H 50/50* (2018.01); *G16H 40/60* (2018.01); *A61N 1/0534* (2013.01)

(58) Field of Classification Search
None
See application file for complete search history.

(56) References Cited

U.S. PATENT DOCUMENTS

| | | | |
|---|---|---|---|
| 2006/0017749 A1 | 1/2006 | McIntyre et al. | |
| 2008/0123922 A1 | 5/2008 | Gielen et al. | |

(Continued)

FOREIGN PATENT DOCUMENTS

| | | | | |
|---|---|---|---|---|
| CN | 103228210 B | * | 8/2016 | ............. A61B 34/20 |
| CN | 106345056 A | | 1/2017 | |
| WO | 2019072829 A1 | | 4/2019 | |

OTHER PUBLICATIONS

Princich, Juan Pablo, M.D., et al. "Rapid and Efficient Localization of Depth Electrodes and Cortical Labeling using Free and Open Source Medical Software in Epilepsy Surgery Candidates." Frontiers in Neuroscience (2013): n/a. ProQuest. Web. Jun. 6, 2023. (Year: 2013).*

(Continued)

*Primary Examiner* — Lena Najarian

(57) ABSTRACT

A method for simulating a deep-brain stimulation in a computer-assisted platform that includes providing to a (Continued)

neurosurgeon, through a man-machine interface, visual information of a pre-operative situation, including a representation of a brain. The method also includes monitoring inputs of said neurosurgeon on the man-machine interface, until a trajectory is determined between an entry point and a target for the placement of an electrode. The method further includes comparing said trajectory to a set of previously-established trajectories for the pre-operative situation, so as to determine an overall measurement representative of a quality of the trajectory compared to the previously-established trajectories.

10 Claims, 1 Drawing Sheet

(56) References Cited

U.S. PATENT DOCUMENTS

| 2014/0003696 A1 | 1/2014 | Taghva |
| 2015/0351860 A1 | 12/2015 | Piron et al. |
| 2017/0123487 A1 | 5/2017 | Hazra et al. |
| 2017/0148213 A1 | 5/2017 | Thomas et al. |
| 2019/0209245 A1* | 7/2019 | Sparks ............... G06T 19/003 |

OTHER PUBLICATIONS

Foreign Communication from a Related Counterpart Application, International Search Report and Written Opinion dated Oct. 9, 2018, International Application No. PCT/EP2018/077446 filed on Dec. 14, 2018.

Caroline Essert et al: "Automatic computation of electrode trajectories for Deep Brain Stimulation: a hybrid symbolic and numerical approach", International Journal of Computer Assisted Radiology and Surgery; A Journal for Interdisciplinary Research, Development and Applications of Image Guided Diagnosis and Therapy, Springer, Berlin, DE, vol. 7, No. 4, Aug. 25, 2011 (Aug. 25, 2011), pp. 517-532, XP035082994, ISSN: 1861-6429, DOI: 10.1007/S11548-011-0651-8.

* cited by examiner

PROFICIENCY ASSESSMENT SYSTEM AND METHOD FOR DEEP BRAIN STIMULATION (DBS)

CROSS-REFERENCE TO RELATED APPLICATIONS

The present application is a filing under 35 U.S.C. 371 as the National Stage of International Application No. PCT/EP2018/077446, filed Oct. 9, 2018, entitled "PROFICIENCY ASSESSMENT SYSTEM AND METHOD FOR DEEP BRAIN STIMULATION (DBS)," which claims priority to European Application No. 17306370.2 filed with the European Patent Office on Oct. 11, 2017, both of which are incorporated herein by reference in their entirety for all purposes.

FIELD OF THE INVENTION

The invention concerns the field of neurosurgery and in particular the planning of a neurosurgical operation for deep brain stimulation, DBS. It relates to a tool for simulating such an operation and for training clinicians in its planning.

BACKGROUND OF THE INVENTION

Deep Brain Stimulation (DBS) is a surgical operation involving the placement of thin electrodes (or «neurostimulator») into well-determined specific targets on the basal ganglia, so as to deliver high-frequency electrical impulses. Deep brain stimulation has proven to be a great success due to its minimally invasiveness, its reversibility and its powerful therapeutic effects. In particular, it has resulted in a renaissance of an alternative way for treatment of Parkinson's disease but also essential tremor, dystonia, obsessive-compulsive disorders (OCD), chronic pain, etc.

The procedure comprises inserting the electrodes into the basal ganglia through small burr holes in the skull, based on a plan created in advance by a neurosurgeon from MRI (Magnetic Resonance Imaging) images.

During this phase, the target point is chosen in the registered images based on the particular disease to have the optimal therapeutic effect. Subsequently, the entry point is chosen such that the linear trajectory from the entry point to the target point poses the least risk to the patient.

Recent studies have however shown that inaccurate electrode placement can reduce the therapeutic effects and have significant adverse effects. Such inaccuracy may be the result of several factors including imperfect surgical planning due to difficulties in localizing anatomical and functional targets.

Recently, several different software solutions have been proposed for facilitating the planning processes for the neurosurgeons. In 2006, Guo et al. introduced one of the first DBS planning platforms, which offers automated image registration, anatomical segmentation, and visualization for target localization. This tool is described in the article «Visualization and navigation system development and application for stereotactic deep-brain neurosurgeries», in Computer Aided Surgery, 11, pp. 231-239. This system demonstrated improved targeting accuracy over traditional methods. Since then, the tools available on the market have further improved and are well-accepted and widespread in clinical practice.

In addition to these software solutions for facilitating the DBS planning process, several algorithms have been proposed for automatically determining a suitable electrode trajectory for DBS. These methods typically rely on anatomic segmentation of the brain and attempt to find the trajectory, or the set of trajectories, which optimize a cost function. The cost function is usually based on expert consensus and penalizes trajectories which intersect or nearly intersect critical structures inside the brain (e.g. sulci, ventricles . . . ). Such a cost function can be displayed in software tools so as to further help the surgeons.

Complication rate and adverse side-effects, however, are still significantly higher for inexperienced neurosurgeons. This has been particularly well demonstrated in the paper «Deep-brain stimulation: long-term analysis of complications caused by hardware and surgery—experiences from a single centre», of Voges, J. et al., in Journal of Neurology, Neurosurgery & Psychiatry, 2006, 77(7), pp. 868-872.

Consequently, there is a need for neurosurgeons to be trained extensively in order to accurately and reliably plan the DBS operations, despite the help of existing software tools, which facilitate this planning process.

SUMMARY OF THE INVENTION

The object of the present invention is to alleviate at least partly the above mentioned drawbacks.

This object is achieved with a method for simulating a deep-brain stimulation in a computer-assisted platform, comprising steps of:
  providing to a neurosurgeon, through a man-machine interface, visual information of a pre-operative situation, including a representation of a brain;
  monitoring inputs of said neurosurgeon on said man-machine interface, until a trajectory is determined between an entry point and a target for the placement of an electrode;
  comparing said trajectory to a set of previously-established trajectories for said pre-operative situation, so as to determine an overall measurement representative of a quality of said trajectory compared to said previously-established trajectories.

Preferred embodiments comprise one or more of the following features, which can be taken separately or together, either in partial combination or in full combination.
  said overall measurement is based on a set of measurements corresponding to primitive proficiency metrics according to which said trajectory is compared to said set of previously-established trajectories.
  said primitive proficiency metrics comprises
    the angle between said trajectory and a trajectory of said set of previously-established trajectories;
    the distance between said trajectory and a trajectory of said set of previously-established trajectories;
    a trajectory risk, representative of a risk involved by said trajectory;
  the method further comprises comparing other inputs than said trajectory to previously-established inputs, so as to provide measurements according to additional primitive proficiency metrics;
  said overall measurement ($c_i$) for said neurosurgeon (i) is determined by:

$$c_i = \frac{\sum_{j=1}^{N_P} r_{i,j}}{N_E \times N_P}$$

wherein $N_E$ is the number of said previously-established trajectories, $N_P$ is the number of said primitive proficiency metrics and $r_{i,j}$ is the rank of said neurosurgeon among the measurements related to previously-established trajectories for the $j^{th}$ primitive proficiency metric;

a target is provided to said neurosurgeon, and wherein determining said trajectory consists in determining an entry point;

a set of pre-operative situations is provided to said neurosurgeon, and wherein said overall measurement is determined for a first pre-operative situation and for a last pre-operative situation, among said set, so as to compare them for assessing a progress of said neurosurgeon;

some feedbacks are provided to said neurosurgeon through said man-machine interface;

Another subject-matter of the invention consists of a computer program comprising instructions for performing a method as previously defined, when deployed on a data computing unit of a network node.

Another subject-matter of the invention consists of a system for simulating a deep-brain stimulation in a computer-assisted platform, comprising:

a man-machine interface for providing to a neurosurgeon, visual information of a pre-operative situation, including a representation of a brain, and for monitoring inputs of said neurosurgeon on said man-machine interface, until a trajectory is determined between an entry point and a target for the placement of an electrode;

means for comparing said trajectory to a set of previously-established trajectories for said pre-operative situation, so as to determine an overall measurement representative of a quality of said trajectory compared to said previously-established trajectories.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
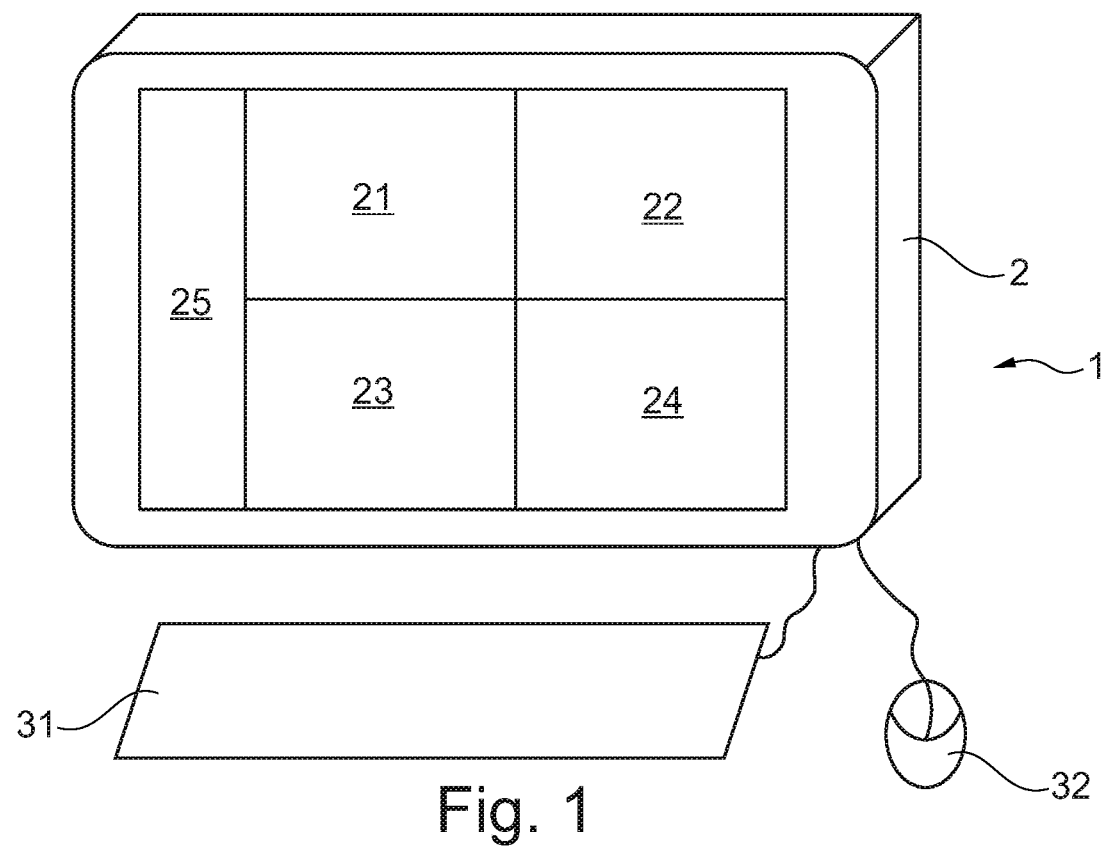
FIG. 1 shows an embodiment for a man-machine interface of a system according to the invention.

Thanks to this invention, the links between master and apprentice or trainee surgeons are enriched by an automatic computer-assisted simulation tool, wherein the behavior of the (apprentice or trainee) surgeon is compared with the recorded behavior of peers or experienced surgeons, so as to provide him/her feedbacks.

These feedbacks are obviously essential for the training of apprentice surgeons, but can also be used by more experienced surgeons to check his/her ability throughout the years.

According to the invention, visual information is provided to the surgeon through a man-machine interface. This visual information relates to a pre-operative situation that the surgeon should face. It includes a representation, or model, of a brain and at least a target for the placement of an electrode.

This man-machine interface as well as the required software elements needed to handle the various information and interact with the surgeon can be implemented by existing software platforms. For instance, the «3D Slicer» product (http://www.slicer.org) can be used for providing an environment enabling medical image computing and visualization. In addition, the DBS planning interface can be based on another software product like e.g. the PyDBS software, which allows patient cases to be readily loaded, visualized and planned. Furthermore, the Perk Tutor platform (http://www.perktutor.org) can be used to capture the planning process, calculate all data and compute resulting measurement(s) as it will be explained later on.

These software tools have been used by the inventors to develop the invention. However, other tools already existing or still to come can also be used, as the principles of the invention are independent of the underlying software platforms and technologies.

This visual information comprises a representation of a brain. More precisely, this representation may correspond to a real past use case, or to a simulated use case.

This representation may consist of one or several images, e.g. provided by magnetic-resonance imaging (MRI), and/or anatomical atlases.

MRI is based on the magnetization properties of atomic nuclei. A powerful, uniform, external magnetic field is employed to align the protons that are normally randomly oriented within the water nuclei of the tissue being examined. This alignment (or magnetization) is next perturbed or disrupted by introduction of an external Radio Frequency energy. The nuclei return to their resting alignment through various relaxation processes and in so doing emit radio-frequency energy.

After a certain period following the initial radio-frequency, the emitted signals are measured. A Fourier transformation is used to convert the frequency information contained in the signal from each location in the imaged area to corresponding intensity levels, which are then displayed as shades of gray in a digital image.

By varying the sequence of RF pulses applied & collected, different types of images are created. Repetition Time (TR) is the amount of time between successive pulse sequences applied to the same slice. Time to Echo (TE) is the time between the delivery of the radio-frequency pulse and the receipt of the echo signal.

The most common Mill sequences are T1-weighted and T2-weighted scans. T1-weighted images are produced by using short TE and TR times. The contrast and brightness of the image are predominately determined by T1 properties of tissue. Conversely, T2-weighted images are produced by using longer TE and TR times. In these images, the contrast and brightness are predominately determined by the T2 properties of tissue.

T1-weighted imaging is used to differentiate anatomical structures mainly on the basis of T1 values, i.e. the scanning parameters are set to minimize T2 relaxations effects (short TR and short TE). Tissues with high fat content (e.g. white matter) appear bright and compartments filled with water (e.g. cerebrospinal fluid) appears dark. Such images are convenient for demonstrating anatomy.

On the other hand, T2-weighted imaging is used to differential anatomical structures mainly on the basis of T2 values, i.e. the scanning parameters are set to minimize T1 relaxation effects (long TR and long TE). Compartments filled with water appear bright and issues with high fat content appear dark. Such images are good for demonstrating pathology since most lesions are associated with an increase in water content.

On FIG. 1 is depicted a possible man-machine interface with which the neurosurgeon can interact with the system according to an embodiment of the invention. This man-machine interface 1 comprises a display unit 2 adapted to provide the neurosurgeon with visual information on the pre-operative situation. Such a situation may be recorded in advance in a database and may be associated with a real case, or with an artificial case constructed for a training purpose.

This visual information includes a representation, or model, of a brain. This representation may consist of one or several digital images. In FIG. 1, the visual information comprises 4 images 21, 22, 23, 24.

Typically, these images are based by T1-weighted and T2-weighted magnetic resonance imaging. They can be built on a combination of such two sources, but also on additional sources like an anatomical atlas, so as to map the 2D data provided by Mill onto a 3D model.

The displayed images 21, 22, 23, 24 can represent the same data but along different projection axis and angle, so as to allow the neurosurgeon to get a spatial understanding of the situation. The interface may furthermore allow him/her to change display parameters and/or move around a 3D representation.

In addition to the images 21, 22, 23, 24, some textual information 25 can also be produced on the display unit 2. This textual information can comprise information regarding the representation of the brain, and, more generally on the pre-operative situation. It can also comprise information regarding the planning process of the deep-brain stimulation, as it will be explained below.

In addition to the representation of the brain, the visual information may also include at least a target for the placement of an electrode, according to some embodiments and/or configurations of the system. For doing so, the target may be computed by algorithmic means or manually set as it will be explained later on, and depending on embodiments of the invention. The target corresponds to a location on the basal ganglia which maximize the therapeutic effect on the disease.

This or these target(s) may be depicted with specific symbols and/or colors, so as to be easily distinguished on the images 21, 22, 23, 24.

The visual information may also depict the trajectories set by the neurosurgeon. Colors may also be used to represent a quality of the planned trajectory.

Interaction means 31, 32 are also available to enable the neurosurgeon to provide inputs that are monitored by the underlying software means to determine a trajectory.

The trajectory consists on an entry point on the skull (or surface of the brain) and a target location on the basal ganglia. The trajectory goes through the cerebral cortex.

Figure 2:
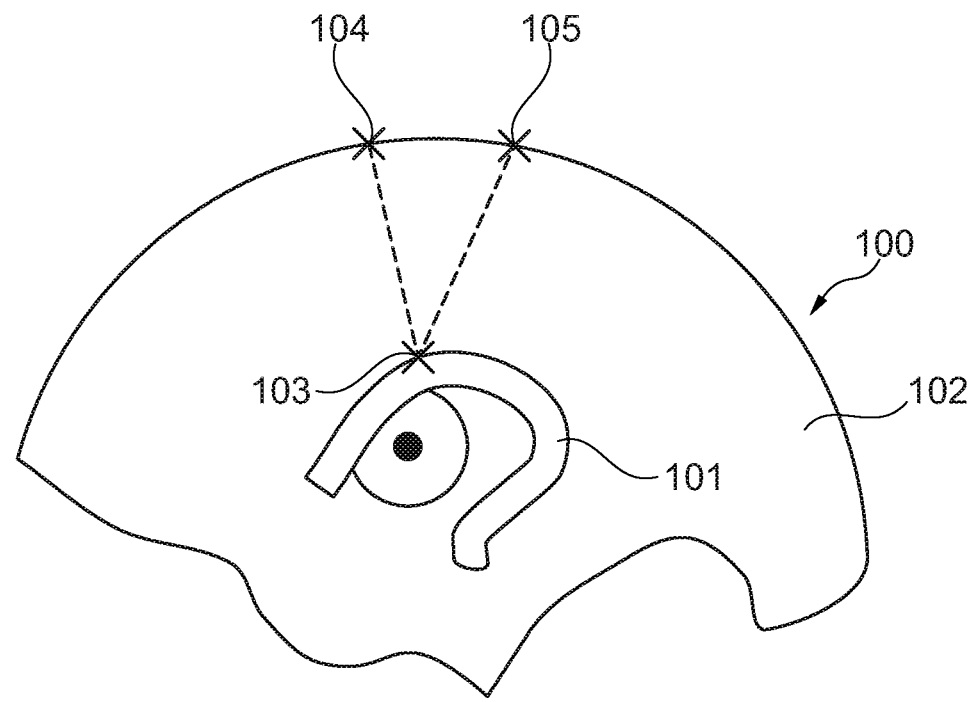
FIG. 2 shows a schematic depiction of a brain and possible trajectories for Deep Brain Stimulation.

FIG. 2 depicts an example of a brain on which a DBS is to be simulated. The brain 100 comprises the basal ganglia 101, on which at least one electrode is to be placed on the target location 103. The determination of this target location is crucial, as it determines its therapeutic effect, and possible side-effects that need to be avoided.

Once this target location is determined, the neurosurgeon then needs to determine a trajectory to reach this target by selecting an appropriate entry point 104, 105 on the surface of the cerebral cortex 102. The choice of the entry point 104, 105 is also crucial and needs to allow the electrode to be inserted throughout the cerebral cortex without intersecting or being too close to some vital areas of the brain.

Thanks to the man-machine interface and the underlying software means, described here-above, the neurosurgeon can try different entry points and trajectories, until s/he determines a final trajectory.

This (final) trajectory determined by the neurosurgeon can then be compared by the software means to a set of previously-established trajectories for the same pre-operative situation. These previously-established trajectories can be stored in a database populated by expert neurosurgeons or peers.

In particular, according to an embodiment of the invention, a comparison can be done with a reference trajectory, which represents an optimal trajectory.

In order to compare two trajectories, several primitive proficiency metrics can be used to assess the trajectory quality, resulting in respective measurements. Furthermore, the riskiness of the trajectory can be assessed relative to critical structures of the brain.

In other words, the system compares the trajectory determined by the neurosurgeon by establishing a set of measurements according to primitive proficiency metrics, and by comparing these measurements with respective measurements established for a set of previously-established trajectories.

Several embodiments can be deployed for performing such a comparison.

According to a preferred embodiment, a non-parametric extension of the z-score normalization method is used. Such a method is for instance described in the article "Support Vector machines improve the accuracy of evaluation for the performance of laparoscopic training tasks" by Allen, B, V. Nistor, E. Dutson, G. Carman, C. Lewis and P. Faloutsos, in *Surg. Endosc.* 24:170-178, 2010.

Each primitive proficiency metric assesses a proficiency of the neurosurgeon in one particular aspect of the DBS planning procedure. None of these metrics may then have enough discriminatory power to distinguish novices from more experienced neurosurgeons. Accordingly, it is further proposed to compute an overall measurement of the planning proficiency of a neurosurgeon by combining measurements based on a set of primitive metrics.

In a typical z-score normalization method, the overall score of a neurosurgeon would be computed by taking a weighted sum of their z-score of each primitive metric relative to the expert neurosurgeon population. Because of the skewed distributions of experts' primitive metrics, however, we use a weighted sum of ranks relative to the expert population.

In particular, an equal weighting scheme is used. Furthermore, the data is normalized by the number of experts $N_E$ and the number of primitive proficiency metrics $N_P$. This normalization enforces that the combined measure of proficiency is independent of the number of experts and number of primitive proficiency metrics.

In practice, the combined, or "overall", measurements $c_i$ of the $i^{th}$ neurosurgeon can be determined according to the following relationship:

$$c_i = \frac{\sum_{j=1}^{N_P} r_{i,j}}{N_E \times N_P}$$

wherein $r_{i,j}$ represent the rank of this neurosurgeon among the measurements of expert neurosurgeons for the $j^{th}$ primitive proficiency metric (in case of ties, the average rank can be used for ordering ties).

Other embodiments are possible to combine measurements according to several primitive proficiency metrics, so as to determine an overall measurement $c_i$, which is representative of a quality of the trajectory determined by the training neurosurgeon, compared to previously-established trajectories. This quality and this measurements determines the proficiency of the training neurosurgeon.

In order to have a meaningful combined measurement $c_i$, appropriate primitive proficiency metrics should be chosen.

In particular, these metrics can comprise:

the angle between the trajectory determined by the training neurosurgeon and the reference trajectory.

the distance between the target determined by the training neurosurgeon and the reference target A trajectory risk, representative of a risk involved by the trajectory determined by the training neurosurgeon. It can be based on segmentations of the target structure, ventricles and sulci. This risk may be computed using the aggregate cost function and weights proposed by Esset et al. in the article "Automatic Comutation of electrode trajectories for Deep Brain Stiumation: a hybrid symbolic and numerical approach", in *In. J. Comput. Assist. Radiol. Surg.* 7:517-532, 2011. This risk value is then in the range [0, 1], wherein a lower cost indicates a safer trajectory.

Furthermore, during the process of determination of this (final) trajectory, the inputs of the neurosurgeon are monitored, so as to capture a full picture of his/her behavior. This enables the systems to not only measure the quality of the determined trajectory, but also the quality of his/her behavior until this determination.

Accordingly, some additional primitive proficiency metrics can be taken into account to capture measurements on this behavior during the planning process. For doing this, some other inputs than the trajectory itself are used.

For instance, they can comprise:

The total elapsed time, which captures the total time it took to the training neurosurgeon to plan the DBS procedure from when he was presented the particular patient case, until the determination of the trajectory.

The number of entry points and target movements. This metric measures the number of different trajectories tried by the training neurosurgeon before determining the final one. This metric is based on the number of separate instances in which the surgeon moved each of the entry and target points.

The entry and target bounding bow. This metric measures how disparate the different trajectories the surgeon tried were. This is based on the volume of the bounding bow containing all attempted entry and target points.

The number of slice crosshair movements. This metric measures how many separate times the surgeon views and interacts with the image slices. This is based on the number of times the surgeon moved the axial, coronal and sagittal slice crosshair.

The path length of slice intersection. This metric measures how many different image slices in each of the axial, coronal and sagittal planes the surgeon viewed. This provides a sense of how much s/he inspected the images during the planning.

Verification of the trajectory. This metric measures whether or not the neurosurgeon has verified that the trajectory does not intersect any of the anatomy using the patient images. In practice, this is calculated as the proportion of the trajectory through which the operator has scrolled in each of the axial, coronal and sagittal slices.

Verification of registration. Because certain anatomies are visible in the T1 MRI image and others in the T2 MRI images, the two imaging modalities must be registered. This metric computes how much the surgeon has checked that the images are registered and the anatomical segmentation is acceptable, based on the extent to which the neurosurgeon has viewed the overlaid images.

This set of primitive proficiency metrics has proved to be efficient and sufficient to determine a meaningful overall measurement representative of the quality of the trajectory and of the proficiency of the training surgeon. However, some other primitive proficiency metrics can be designed in place or in addition of the ones of this set.

In addition, according to an embodiment of the invention, some of these measurements can be provided to the training neurosurgeon through the man-machine interface, e.g. as numeric data displayed as textual information 25. In particular, the distance to reference point, the angle to reference target and the risk of the planned trajectory can be displayed, as feedback, to the training neurosurgeon.

This feedback can assist neurosurgeons, especially trainees, in understanding the clinical situation and their own planning.

In addition to the textual and numeric information, some visual information may be also provided, so as to provide an intuitive sense of a good trajectory.

According to an embodiment of the invention, different amounts and levels of information can be provided according to configuration. This configuration may depend directly on the level of expertise of the training neurosurgeon.

For instance, a training course can be designed according to this scheme and comprise 5 phases. For example, during each phase, the trainee completes two DBS plans: one targeting the subthalamic nucleus (STN) and one targeting the internal part of the globus pallidus (GPI). With the exception of the first phase, the training course is designed to be completed by each trainee on their own, without any instruction.

During the first phase, the trainee is exposed to the entire DBS planning process, as well as all of the feedback metrics that are provided. This phase is intended to allow the trainees to familiarize themselves with the planning software. This phase is supervised and the trainee is encouraged to ask questions about how to use the software.

During the second phase, the trainee must go through the complete DBS planning process and no feedback is provided. This phase is intended to evaluate the trainee's DBS planning proficiency at the beginning of the training course.

During the third phase, the trainee is provided with a pre-planned target point. Thus the trainee only needs to plan the entry point of the trajectory, with feedback provided throughout. This phase is intended to help the trainee learn how to plan the entry point based on the cranial anatomy, under the assumption that the target point has been appropriately identified.

During the fourth phase, the trainee must go through the complete DBS planning process, with feedback provided throughout. This phase is intended to let the trainee practice the entire planning process, learning from the feedback provided on their trajectory quality.

During the fifth phase, the trainee must again go through the complete DBS planning process but with no feedback. This phase is intended to evaluate the trainee's DBS planning proficiency at the end of the training course.

Throughout the training course, all of the measurements are recorded but only a part of them may be displayed to the trainee. The measurements of proficiency at the first phase and last phase can be compared to assess the progress of the trainee.

More generally, by providing to the training neurosurgeon a set of pre-operative situations, it is possible to determine the overall measurements for a first pre-operative situation and for a last pre-operative situation, among said set, so as to compare them for assessing a progress of the neurosurgeon.

The invention has been described with reference to preferred embodiments. However, many variations are possible within the scope of the invention.

The invention claimed is:

1. Method for simulating a deep-brain stimulation in a computer-assisted platform, comprising steps of:
as part of a training process of a training neurosurgeon:
providing to the training neurosurgeon, through a man-machine interface, visual information of a pre-operative situation, including a representation of a brain, wherein the representation of the brain comprises a three-dimensional (3D) representation;
receiving inputs of said training neurosurgeon on said man-machine interface indicating movement around the 3D representation and a change in one or more display parameters of the man-machine interface;
providing via the man-machine interface the movement around the 3D representation and changing the one or more display parameters of the man-machine interface in response to receiving the inputs of said training neurosurgeon indicating the movement around the 3D representation and the change in the one or more display parameters;
monitoring the inputs of said training neurosurgeon on said man-machine interface, until a trajectory is determined between an entry point and a target for placement of an electrode;
comparing said trajectory of said training neurosurgeon to a set of previously-recorded trajectories of other neurosurgeons for said pre-operative situation stored in a database; and
determining an overall measurement representative of a quality of said trajectory of said training neurosurgeon compared to the trajectories of said set of previously-recorded trajectories based on the comparing; and
providing feedback to the training neurosurgeon via the man-machine interface, the feedback comprising textual information including a distance to a reference point, an angle to a reference target, and a risk of a planned trajectory.

2. Method according to claim 1, wherein said overall measurement is based on a set of measurements corresponding to primitive proficiency metrics according to which said trajectory is compared to said set of previously-recorded trajectories.

3. Method according to claim 2, wherein said primitive proficiency metrics comprises
an angle between said trajectory and a trajectory of said set of previously-recorded trajectories;
a distance between said trajectory and a trajectory of said set of previously-recorded trajectories;
a trajectory risk, representative of a risk involved by said trajectory.

4. Method according to claim 1, further comprising comparing other inputs than said trajectory to previously recorded inputs, so as to provide measurements according to additional primitive proficiency metrics.

5. Method according to claim 2, wherein said overall measurement ($c_i$) for said training neurosurgeon (i) is determined by:

$$c_i = \frac{\sum_{j=1}^{N_P} r_{i,j}}{N_E \times N_P}$$

wherein $N_E$ is the number of trajectories of said set of previously-recorded trajectories, $N_P$ is the number of said primitive proficiency metrics and $r_{i,j}$ is the rank of said training neurosurgeon among measurements related to the trajectories of said set of previously-recorded trajectories for a $j^{th}$ primitive proficiency metric of said primitive proficiency metrics.

6. Method according to claim 1, wherein the target is provided to said training neurosurgeon, and wherein determining said trajectory consists in determining the entry point.

7. Method according to claim 1, wherein a set of pre-operative situations is provided to said training neurosurgeon, and wherein said overall measurement is determined for a first pre-operative situation and for a last pre-operative situation, among said set, so as to compare them for assessing a progress of said training neurosurgeon.

8. Method according to claim 1, wherein some feedbacks are provided to said training neurosurgeon through said man-machine interface.

9. Computer program product comprising:
a non-transitory computer storage medium having instructions stored thereon that, when deployed on a data computing unit of a network node, as part of a training process of a training neurosurgeon:
provides to the training neurosurgeon, through a man-machine interface, visual information of a pre-operative situation, including a representation of a brain that comprises a three-dimensional (3D) representation;
receives inputs of said training neurosurgeon on said man-machine interface indicating movement around the 3D representation and a change in one or more display parameters of the man-machine interface;
provides via the man-machine interface the movement around the 3D representation and changes the one or more display parameters of the man-machine interface in response to receiving the inputs of said training neurosurgeon indicating the movement around the 3D representation and the change in the one or more display parameters;
monitors the inputs of said training neurosurgeon on said man-machine interface, until a trajectory is determined between an entry point and a target for placement of an electrode;
compares said trajectory of said training neurosurgeon to a set of previously-recorded trajectories of other neurosurgeons for said pre-operative situation stored in a database;
determines an overall measurement representative of a quality of said trajectory of said training neurosurgeon compared to the trajectories of said set of previously-recorded trajectories based on the comparing; and
provides feedback to the training neurosurgeon via the man-machine interface, the feedback comprising textual information including a distance to a reference point, an angle to a reference target, and a risk of a planned trajectory.

10. System for simulating a deep-brain stimulation in a computer-assisted platform, comprising:

a man-machine interface for providing to a training neurosurgeon, visual information of a pre-operative situation, including a representation of a brain that comprises a three-dimensional (3D) representation, and for monitoring inputs of said training neurosurgeon on said man-machine interface, until a trajectory is determined between an entry point and a target for placement of an electrode;

a database storing a set of previously-recorded trajectories of other neurosurgeons for said pre-operative situation; and an application stored in a non-transitory memory that, when executed by a processor, during a training process of the training neurosurgeon:

receives the inputs of said training neurosurgeon on said man-machine interface, wherein the inputs indicate movement around the 3D representation and a change in one or more display parameters of the man-machine interface, provides via the man-machine interface the movement around the 3D representation and changes the one or more display parameters of the man-machine interface in response to receiving the inputs of said training neurosurgeon indicating the movement around the 3D representation and the change in the one or more display parameters, compares said trajectory of said training neurosurgeon to the set of previously-recorded trajectories of other neurosurgeons for said pre-operative situation from the database, determines an overall measurement representative of a quality of said trajectory of said training neurosurgeon compared to said previously-recorded trajectories based on the comparison, and provides feedback to the training neurosurgeon via the man-machine interface, the feedback comprising textual information including a distance to a reference point, an angle to a reference target, and a risk of a planned trajectory.

\* \* \* \* \*